United States Patent
Winter et al.

(10) Patent No.: US 6,172,168 B1
(45) Date of Patent: Jan. 9, 2001

(54) PROCESS FOR THE PREPARATION OF 1-OLEFIN POLYMERS

(75) Inventors: Andreas Winter, Kelkheim; Walter Spaleck, Bochum, both of (DE)

(73) Assignee: Targor GmbH (DE)

( * ) Notice: Under 35 U.S.C. 154(b), the term of this patent shall be extended for 0 days.

(21) Appl. No.: 09/461,475

(22) Filed: Dec. 14, 1999

Related U.S. Application Data

(62) Division of application No. 08/846,667, filed on May 1, 1997, now Pat. No. 6,017,841, which is a continuation of application No. 08/477,854, filed on Jun. 7, 1995, now Pat. No. 5,661,096, which is a continuation of application No. 08/387,007, filed on Feb. 10, 1995, now abandoned, which is a continuation of application No. 07/842,796, filed on Feb. 27, 1992, now abandoned, which is a continuation of application No. 07/750,764, filed on Aug. 22, 1991, now Pat. No. 5,416,178, which is a continuation of application No. 07/518,239, filed on May 4, 1990, now abandoned, which is a continuation-in-part of application No. 07/229,095, filed on Aug. 5, 1988, now Pat. No. Des. 318,325, which is a continuation of application No. 07/228,546, filed on Aug. 4, 1988, now abandoned.

(30) Foreign Application Priority Data

Aug. 6, 1987 (DE) ................................. 37 26 067

(51) Int. Cl.$^7$ ..................................... C08F 4/52
(52) U.S. Cl. .................... 526/127; 526/160; 526/166; 526/943; 502/103; 502/117
(58) Field of Search ................... 526/127, 166, 526/160, 943; 502/103, 117

(56) References Cited

U.S. PATENT DOCUMENTS

| | | | |
|---|---|---|---|
| 4,522,982 | 6/1985 | Ewen | 525/240 |
| 4,530,914 | 7/1985 | Ewen et al. | |
| 4,536,484 | 8/1985 | Lacombe et al. | 502/62 |
| 4,542,199 | 9/1985 | Kaminsky et al. | 526/160 |
| 4,701,432 | 10/1987 | Welborn, Jr. | 502/113 |
| 4,752,597 | 6/1988 | Turner | 502/104 |
| 4,767,735 | 8/1988 | Ewen et al. | 502/109 |
| 4,769,510 | 9/1988 | Kaminsky et al. | 585/512 |
| 4,791,180 | 12/1988 | Turner | 526/160 |
| 4,794,096 | * 12/1988 | Ewen | 502/117 |
| 4,808,561 | 2/1989 | Welborn, Jr. | 502/104 |
| 4,841,004 | * 6/1989 | Kaminsky et al. | 526/160 |
| 4,849,487 | 7/1989 | Kaminsky et al. | 526/351 |
| 4,897,455 | * 1/1990 | Born, Jr. | 526/129 |
| 4,931,417 | 6/1990 | Miya et al. | |
| 4,933,403 | 6/1990 | Kaminsky et al. | 526/160 |
| 4,937,299 | 6/1990 | Ewen et al. | 526/119 |
| 5,017,714 | 5/1991 | Welborn, Jr. | 556/12 |
| 5,084,534 | 1/1992 | Welborn, Jr. et al. | 526/160 |
| 5,103,030 | 4/1992 | Rohrmann et al. | 526/12 |
| 5,120,867 | 6/1992 | Welborn, Jr. | 556/12 |
| 5,132,381 | 7/1992 | Winter et al. | |
| 5,314,973 | 5/1994 | Welborn, Jr. | 526/126 |
| 5,416,178 | 5/1995 | Winter et al. | 526/160 |
| 5,441,920 | 8/1995 | Welborn, Jr. | |

FOREIGN PATENT DOCUMENTS

| | | |
|---|---|---|
| 029 108 | 12/1984 | (AU) . |
| 058 914 | 12/1986 | (AU) . |
| 067 773 | 6/1987 | (AU) . |
| 079 165 | 4/1988 | (AU) . |
| 020 435 | 2/1989 | (AU) . |
| 627588 | 9/1961 | (CA) . |
| 1 317 411 | 5/1993 | (CA) . |
| 37 26 067 | 2/1989 | (DE) . |
| 0 127 530 | 12/1984 | (EP) . |
| 0 128 046 | 12/1984 | (EP) . |
| 0 129 368 | 12/1984 | (EP) . |
| 0 185 918 | 7/1986 | (EP) . |
| 0 197 319 | 10/1986 | (EP) . |
| 0 206 794 | 12/1986 | (EP) . |
| 0 226 463 | 6/1987 | (EP) . |
| 0 232 595 | 8/1987 | (EP) . |
| 0 260 999 | 3/1988 | (EP) . |
| 0 284 707 | 10/1988 | (EP) . |
| 0 284 708 | 10/1988 | (EP) . |
| 0 302 424 | 2/1989 | (EP) . |
| 0 320 762 | 6/1989 | (EP) . |
| 2 539 133 | 7/1984 | (FR) . |
| 121708 | 6/1987 | (JP) . |
| 63-192874 | 8/1988 | (JP) . |
| 63-295607 | 12/1988 | (JP) . |

OTHER PUBLICATIONS

Gianetti et al., *Journal of Polymer Science*, Polymer Chemistry Div., vol. 23, 2117–2183 (1985).

Moore, *Physical Chemistry*, Prentice Hall, NJ (1955), p. 116.

Kaminsky et al., "Olefinpolymerization with Highly Active Soluble Zirconium Compounds Using Aluminoxane as Cocatlyst", Makromol, Chem., Macromol. Symp. 3, pp. 377–387 (1986).

Ewen et al., Crystal Structures and Stereospecific Propylene Polymerization witn Chiral Hafnium Metallocene Catalysts, J. Am. Chem Soc. 109, pp. 6544–6545 (1987).

Kaminsky et al., "Transition Metals and Organometallics as Catalysts for Olefin Polymerization", Proceedings of an International Symposium, Hamburg, Sep. 21–24, 1987, pp. 281–289 (1988).

Schwenlein et al. Journal of Organometallic Chemistry, 254 (1983) 69–73.

Grant & Hackh's Chemical Dictionary ($3^{rd}$ Ed.), p. 192.

* cited by examiner

Primary Examiner—David W. Wu
Assistant Examiner—Ling-Siu Choi
(74) Attorney, Agent, or Firm—Connolly Bove Lodge & Hutz LLP

(57) ABSTRACT

In the case of Ziegler catalysts based on a metallocene as the transition metal component and an aluminoxane as the activator, preactivation of the metallocene with the aluminoxane results in a considerable increase in the activity of the catalyst system. Furthermore, 1-olefin polymers of a high degree of isotacticity and having compact, spherical particles, a very narrow particle size distribution and a high bulk density are obtained by means of a catalyst system of this type.

16 Claims, No Drawings

PROCESS FOR THE PREPARATION OF 1-OLEFIN POLYMERS

This application is a divisional of Ser. No. 08/846,667, filed May 1, 1997, now U.S. Pat. No. 6,017,841, which is a continuation of application Ser. No. 08/477,854, filed Jun. 7, 1995, now U.S. Pat. No. 5,661,096, which is a continuation of application Ser. No. 08/387,007, filed Feb. 10, 1995, now abandoned, which is a continuation of application Ser. No. 07/842,796, filed Feb. 27, 1992, now abandoned, which is a continuation of application Ser. No. 07/750,764, filed Aug. 22, 1991 and now U.S. Pat. No. 5,416,178, which is a continuation of application Ser. No. 07/518,239, filed May 4, 1990 and now abandoned, and is also a continuation-in-part of application Ser. No. 07/229,095, filed Aug. 5, 1988 and is now U.S. Pat. No. D. 318,325 issued Jul. 16, 1991, and which in turn is a continuation of application Ser. No. 07/228,546, filed Aug. 4, 1988, and now is abandoned. Our U.S. application Ser. No. 490,833, filed Mar. 8, 1990, now U.S. Pat. No. 5,132,381, issued Jul. 21, 1992, discloses technologically related matter.

The invention relates to a process for the preparation of 1-olefin polymers having a high degree of isotacticity and an advantageous particle size distribution.

In recent times supported catalysts in which transition metal compounds have been applied, together with suitable electron donors, to supports, for example magnesium chloride, have been used for the preparation of polyolefins having a high degree of isotacticity. Aluminum alkyls are used as activators in the polymerization reaction and donors, such as ethyl benzoate or $Ph_2 Si(OR)_2$, are used as stereo regulators to poison non-stereospecific centers.

Since these catalysts consist mainly of $MgCl_2$, relatively high chlorine contents of 30–300 pps are found in the polymers prepared with them, unless these residues are removed by a special after-treatment.

Soluble Ziegler catalysts based on a bis-(cyclopentadienyl)-zirconium alkyl or halide in combination with oligomeric aluminoxanes area also known. These catalysts make it possible to polymerize ethylene and propylene with a moderate activity, but no isotactic polypropylene is obtained.

It is also known of the catalyst system bis-(cyclopentadienyl)-titaniumdiphenyl/methyl aluminoxane that it is capable of converting polypropylene into stereo block polymers, i.e. polypropylene having relatively long isotactic sequences (cf. U.S. Pat. No. 4,522,982). Important disadvantages of this catalyst system are the unsuitability for large scale industry of the polymerization temperatures (0° to −60° C.) and the unsatisfactory activity of the catalyst.

Finally, it is possible to prepare isotactic polypropylene in a suspension polymerization by means of a stereo-rigid and chiral zirconium compound, together with an aluminoxane (cf. EP-A 185,918=U.S. Ser. No. 801,683). The polymer has a narrow molecular weight distribution, which is advantageous for certain fields of use, for example for high-speed injection molding. At the same time the catalyst system has a number of drawbacks. Owing to the low activity, an involved purification of the polymer is required to remove the large residual amounts of catalyst. The bulk density of the polymer is too low and the particle morphology and the particle size distribution are unsatisfactory. In addition, the polymerization is carried out in toluene which has to be purified and freed from moisture and oxygen in a very expensive manner.

It was required to find a catalyst which does not have the disadvantages of the known catalyst.

It has been found that a preactivation of the metallocene by means of an aluminoxane effects a considerable increase in the activity of the catalyst system and an improvement in the particle morphology of the polymer.

The invention therefore relates to a process for the preparations of a 1-olefin polymer by polymerizing a 1-olefin of the formula $R—CH=CH_2$ in which R is an alkyl group having 1 to 28 carbon atoms or copolymerizing these olefins together with ethylene at a temperature from −60 to 200° C., under a pressure of 0.5 to 60 bar, in solution, in suspension or in the gas phase and in the presence of a catalyst which is composed of a metallocene as the transition metal compound and an aluminoxane as the activator, which comprises carrying out the polymerization in the presence of a catalyst in which the transition metal component has been preactivated for 5 minutes to 60 hours, at a temperature from −78 to 100° C., by means of an aluminoxane of the formula IV

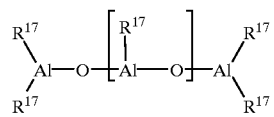

(IV)

for the linear type and/or of the formula V

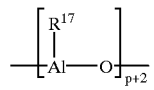

(V)

for the cyclic type, $R^{17}$ in the formulae IV and V being a $C_1$–$C_6$-alkyl group and p being an integer from 2 to 50, and the activator also being an aluminoxane of the formulae IV and/or V.

A variety of metallocene catalysts can be employed for the process according to the invention.

Stereo-rigid, chiral metallocenes are used for the preparation of highly isotactic poly-1-olefins. These metallocenes have the formula I

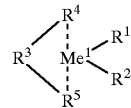

(I)

In this formula $Me^1$ is a metal of group IV b or V b of the periodic system of the elements, i.e.. titanium, zirconium, hafnium, vanadium, niobium, or tantalum, preferably titanium or zirconium and particularly zirconium.

$R^1$ and $R^2$ are identical or different and denote a $C_1$–$C_{10}$-alkyl group, preferably a $C_1$–$C_3$-alkyl group, a $C_6$–$C_{10}$-aryl group, preferably a $C_6$–$C_8$-aryl group, a $C_2$–$C_{10}$-alkenyl group, preferably a $C_2$–$C_4$-alkenyl group, a $C_7$–$C_{40}$-aralkyl group, preferably a $C_7$–$C_{10}$-aralkyl group, a $C_8$–$C_{40}$-arylalkenyl group, preferably a $C_8$–$C_{12}$-arylalkenyl group or a halogen atom, preferably chlorine.

$R^3$ is a linear $C_1$–$C_4$, preferably $C_1$–$C_3$, hydrocarbon radical or a cyclic $C_4$–$C_6$ hydrocarbon radical; these hydrocarbon radicals can contain at least one heteroatom as a bridge unit in the chain. The bridge $R^3$ can also be composed only of heteroatoms.

Examples of single-membered bridge units are —$CR_2^6$—, —O—, —S—, —SO—, —Se—, —SeO—, —$NR^6$—, —$PR^6$—, $AsR^6$—, —$BR^6$—, —$ALR^6$—, —$SiR_2^6$— and —$GeR_2^6$—, $R^6$ being a hydrogen atom, a $C_6$–$C_{10}$-aryl group, preferably a $C_6$–$C_8$-aryl group, a $C_1$–$C_{10}$-alkyl group, preferably a $C_1$–$C_4$-alkyl group, a $C_2$–$C_{10}$-alkenyl group, preferably a $C_2$–$C_6$-alkenyl group, a $C_7$–$C_{40}$-aralkyl group, preferably a $C_7$–$C_{10}$-aralkyl group, a $C_8$–$C_{40}$-arylalkenyl group, preferably a $C_8$–$C_{12}$-arylalkenyl group or a halogen atom, preferably chlorine. The bridge units containing —$CR_2^6$— and silicon and sulfur are preferred.

Examples of two-membered bridge units are —$(CR_2^6)_2$—, —SS—, —SeSe—, —$SiR_2^6SiR_2^6$—, —$SiR_2^6CR_2^6$—.

Examples of multi-membered bridge units are —$(CR_2^6)_3$—, —$(CR_2^6)_4$—, —$SiR_2^6OSiR_2^6$—, —$SiR_2^6(CR_2^6)_nSiR_2^6$—, —$SiR_2^6(CR_2^6)_n$—, —$S(CR_2^6)_nS$—, —$S(CR_2^6)_n$—, —$NR^6(CR_2^6)_nNR$—, —$NR^6(CR_2^6)_n$—, —$PR^6(CR_2^6)_nPR^6$—, —$PR^6(CR_2^6)_n$— in which n=1 or 2 or —$ALR^6DAlR^6$—, $R^6$ having the meaning mentioned above. Bridge units containing —$(CR_2^6)_2$—, —$(CR_2^6)_3$— and silicon and sulfur are preferred.

$R^4$ and $R^5$ are identical or difference, preferably identical. They are mononuclear or multinuclear hydrocarbon radicals which, together with the central atom, can form a sandwich structure. Examples of radicals of this type are the indenyl, tetrahydroindenyl or cyclopentadienyl group and heteroaromatic ligands. Metallocenes which are particularly preferred are bisindenylzirconius dichlorides.

The optically active metallocenes are employed in the form of a racemate. The pure D-form or L-form can, however, also be used. An optically active polymer can be prepared by means of these pure stereoisomeric forms. However, the meso-form of the metallocenes must be removed, since the active center for polymerization (the metal atom) in these compounds is no longer chiral owing to mirror symmetry at the central metal.

The separation of the stereoisomers is known in principle (H. H. Brintzinger et al. Journal of Organometallic Chemistry, 232 (1982) 233 and 328 (1987)87).

The stereo-rigid, chiral metallocenes described above can be prepared by the following scheme of reactions:

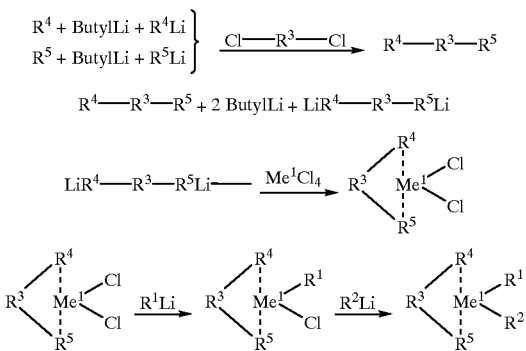

A metallocene of the formula II

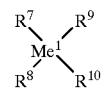

(II)

is employed for the polymerization, according to the invention, of 1-olefins to give stereo-block polymers. In this formula $Me^1$ has the abovementioned meaning.

$R^7$ and $R^8$ are identical or different and denote a halogen atom, $C_1$–$C_{10}$-alkyl, $C_6$–$C_{10}$-aryl, $C_2$–$C_{10}$-alkenyl, $C_7$–$C_{40}$-arylalkyl, $C_7$–$C_{40}$-alkylaryl or $C_8$–$C_{40}$-alkenylaryl.

$R^9$ and $R^{10}$ are identical or different and denote a substituted cyclopentadienyl radical, this radical containing one or more centers of chirality and having been formed by the reaction of an alkali metal cyclopentadienide with a sulfonic acid ester of a chiral alcohol.

In formula II $Me^1$ is preferably zirconium and $R^7$ and $R^8$ preferably denote a halogen atom or an alkyl group, preferably methyl and particularly a chlorine atom. $R^9$ and $R^{10}$ are formed by the reaction of an alkali metal cyclopentadienide, preferably sodium cyclopentadienide, and a sulfonic acid ester of, for example, one of the following chiral alcohols:

Thujyl alcohol; neothujyl alcohol; cis-, trans-sabinol; 2,5-dimethyl-4-vinyl-2,5-hexadien-1-ol; lavandulol; isopulegol; neoisopulegol; cis-, trans-pulegol; isomenthol; neomenthol; neoisomenthol; menthol; cis-, trans-$\Delta^1(7)$-p-menthen-2-ol; cis-, trans-$\Delta^1(7)8$-p-menthadien-2-ol; dihydrocarveol; neodihydrocarveol; isodihydrocarveol; neoisodihydrocarveol; carvomenthol; neoisocarvomenthol; isocarvomenthol; neocarvomenthol; perilla alcohol; phellandrol; butan-2-ol; cycloisolongifolol; isolongifolol; 2-methyl-butanol; octan-2-ol; pentan-2-ol; phenylethanol; hydroxycitrolellal; hydroxycitrolellol; cis-, trans-myrtenol; 2,6-dimethyloct-3-ene-2,8-diol, 2,6-dimethyloct-1-ene-3,8-diol; dihydrocitrouellol; citrouellol, 2,6-dimethylocta-2,7-dien-4-ol; 2,6-dimethylocta-1,7-dien-3-ol; $\Delta^{1,8}$-p-mentadien-9-ol; $\Delta^1$-p-menthen-9-ol; cis-, trans-sobrerol; cis-m-menthan-5-ol; $\therefore^{4/10}$caren-5-ol; $\Delta^3$-caren-2-ol; caren-3-ol; isocaran-3-ol; neocaran-3-ol; neoiso-caran-3-ol; $\alpha,\beta$-fenchol; borneol; isoborneol; cis-, trans-myrtanol; neoverbanol; neoisoverbanol; cis-, trans-chrysanthenol; cis-, trans-verbenol; isoverbanol; cis-, trans-pinocarveol; pinocampheol; neopinocampheol; isopinocampheol; neoisopinocampheol and methylnopinol.

It is particularly preferable to employ the cyclic members of these chiral alcohols. Neomenthol is particularly preferred. Thus the metallocene compound which is particularly preferably used is bis-neomeuthylcyclopentadienyl-zirconium chloride.

The preparation of these compounds can, for example, be effected in the following manner.

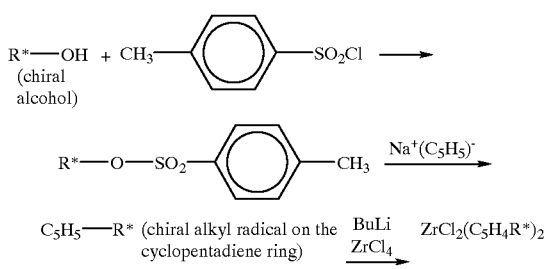

Metallocenes of the formula III

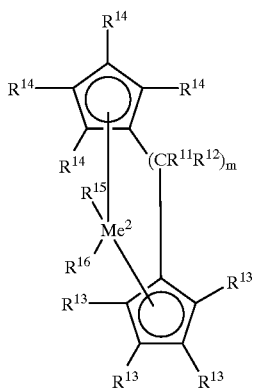

(III)

are also suitable for the preparation of stereo-block polymers. In this formula, $Me^2$ is a metal of group IVb, Vb or VIb of the periodic system, for example titanium, zirconium, hafnium, vanadium, chromium, molybdenum or tungsten, preferably titanium and zirconium.

$R^{11}$ and $R^{12}$ are identical or different and denote $C_1$–$C_{10}$-alkyl, $C_6$–$C_{10}$-aryl, $C_2$–$C_{10}$-alkenyl or $C_7$–$C_{40}$-aralkyl, preferably phenyl, ethyl or methyl, particularly methyl.

$R^{13}$ and $R^{14}$ are identical or different and denote a hydrogen atom or a methyl group, preferably a hydrogen atom.

$R^{15}$ and $R^{16}$ are also identical or different and denote a halogen atom, such as chlorine, bromine or iodine, $C_1$–$C_{10}$-alkyl, $C_6$–$C_{10}$-aryl, $C_2$–$C_{10}$-alkenyl, $C_7$–$C_{40}$-arylalkyl or $C_8$–$C_{40}$-arylalkenyl, preferably methyl or chlorine, particularly chlorine.

m is an integer from 1 to 4, preferably 2.

The metallocene compound which is particularly preferably employed is tetramethylethylenebis(cyclopentadienyl)-titanium dichloride. This type of compound can be prepared, for example, by reductive coupling of 6,6-dimethyl-fulvene using sodium amalgam, sodium anthracenide or magnesium metal/$CCl_4$ as the reducing agent, followed by reacting the anionic tetramethyldicyclopentadienylethane compound with $TiCl_4$ or $ZrCl_4$.

Before being employed in the polymerization reaction, the metallocene is pre-activated by means of an aluminoxane. This aluminoxane is a compound of the formula IV

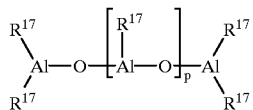

(IV)

for the linear type and/or the formula V

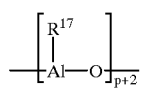

(V)

for the cyclic type. In these formulae, $R^{17}$ denotes a $C_1$–$C_6$-alkyl group, preferably methyl, ethyl or isobutyl, especially methyl, and p is an integer from 2 to 50, preferably 15 to 30.

The aluminoxane can be prepared in various ways.

In one of the processes, finely powdered copper sulfate-pentahydrate is suspended in toluene and sufficient aluminum trialkyl for about 1 mole of $CuSO_4$. $5H_2O$ to be available for every 4 aluminum atoms is added to it, in a glass flask, under an inert gas and at about −20° C. After slow hydrolysis with elimination of alkane, the reaction mixture is kept at room temperature for 24 to 48 hours, in the course of which it must, if necessary, be cooled, so that the temperature does not exceed 30° C. The aluminoxane dissolved in the toluene is then freed from the copper sulfate by filtration, and the toluene is distilled off in vacuo. It is assumed that in this process of preparation the low-molecular aluminoxanes undergo a condensation reaction to give higher oligomers with the elimination of aluminum trialkyl.

Aluminoxanes are also obtained if an aluminum trialkyl, preferably aluminum trimethyl, dissolved in an inert aliphatic or aromatic solvent, preferably heptane or toluene, is reacted at a temperature from 31 20 to 100° C. with aluminum salts, preferably aluminum sulfate, containing water of crystallization. In this process, the ratio by volume between the solvent and the aluminum alkyl used is 1:1 to 50:1—preferably 5:1—and the reaction time, which can be controlled by elimination of the alkane, is 1 to 200 hours—preferably 10 to 40 hours.

Aluminum salts containing water of crystallization which are used particularly are those which have a high content of water of crystallization. Hydrated aluminum sulfate is particularly preferred, above all the compounds $Al_2(SO_4)_3 \cdot 18H_2O$ and $Al_2(SO_4)_3 \cdot 16H_2O$, which have the particularly high content of water of crystallization of 16 to 18 moles of $H_2O$/mole of $Al_2(SO_4)_3$.

The preactivation is carried out in solution. It is preferable to dissolve the metallocene in a solution of the aluminoxane in an inert hydrocarbon. Suitable inert hydrocarbons are aliphatic or aromatic hydrocarbons.

It is preferable to use toluene.

The concentration of the aluminoxane in the solution is within the range from approx. 1% by weight to the saturation limit, preferably from 5 to 30% by weight, in each case relative to the total solution. The metallocene can be employed in the same concentration, but it is preferably employed in an amount of $10^{-4}$–1 mole per mole of aluminoxane. The preactivation time is 5 minutes to 100 hours, preferably 5 to 60 minutes and particularly 10 to 20 minutes.

A considerably longer preactivation is possible, but its effect is normally neither to increase the activity nor to reduce it, though it can be entirely appropriate for storage purposes.

The preactivation is carried out at a temperature from −78 to 100° C., preferably 0 to 70° C.

The preactivation can be carried out either with the exclusion of light or with irradiation by light, since the metallocenes, which, as a rule, are light-sensitive, are stabilized by the aluminoxane. Nevertheless, it is preferable, particularly in the case of prolonged preactivation times and in the case of particularly sensitive metallocenes substituted by heteroatoms, to exclude direct irradiation by light.

The second component of the catalyst to be used in accordance with the invention is an aluminoxane of the formulae IV and/or V. It is preferably to use the same aluminoxane for the preactivation and for the polymerization.

The catalyst to be used in accordance with the invention is employed for the polymerization of 1-olefins of the formula R—CH=$CH_2$ in which R denotes an alkyl radical having 1 to 28 carbon atoms, preferably 1 to 10 carbon atoms and particularly 1 carbon atom, for example propylene, 1-butene, 1-hexane, 4-methylpent-1-ene or 1-octen. Propylene is particularly preferred. The catalyst is also employed for the copolymerization of these olefins with one another and with ethylene, it being possible to copolymerize more than 50% by weight of ethylene.

The polymerization is carried out in a known manner in solution, in suspension or in the gas phase, continuously or discontinuously and in a single stage or in several stages and at a temperature from −60 to 200, preferably −20 to 120, in particular −20 to 80° C. The pressure is 0.5 to 60 bar. Polymerization within the pressure range from 5 to 60 bar, which is of particular industrial interest, is preferred.

In the polymerization, the metallocene compound is employed in a concentration, relative to the transition metal, of $10^{-3}$ to $10^{-7}$, preferably $10^{-4}$ to $10^{-6}$, mole of transition metal per $dm^3$ of solvent or per $dm^3$ of reactor volume. The aluminoxane is used in a concentration of $10^{-4}$ to $10^{-1}$ mole, preferably $10^{-3}$ to $10^{-2}$ mole, per $dm^3$ of solvent or per $dm^3$ of reactor volume. In principle, however, higher concentrations are also possible. It is advantageous first to stir the aluminoxane together with the liquid phase in the polymerization for a few minutes before the metallocene is added to the polymerization system. The stirring time is preferably 10 to 30 minutes. It is also possible, however, to stir for a shorter period without losses of a major character; a longer stirring time has no appreciable effect on the result of the polymerization.

The polymerization is carried out in an inert solvent which is customary for the Ziegler low-pressure process, for example in an aliphatic or cycloaliphatic hydrocarbon; examples of such hydrocarbons which may be mentioned are butane, pentane, hexane, heptane, isooctane, cyclohexane or methylcyclohexane. It is also possible to use a gasoline or hydrogenated diesel oil fraction which has been carefully freed from oxygen, sulfur compounds and moisture. Toluene can also be used. It is preferably to employ the monomer to be polymerized as solvent or suspending agent. The molecular weight of the polymer can be controlled in a known manner; hydrogen is preferably used for this purpose. The polymerization time is optional, since the catalyst system to be used in accordance with the invention displays only a slight time-dependent decrease in polymerization activity.

The process according to the invention makes it possible to prepare polymer powders composed of compact, spherical particles having a very narrow particle size distribution and a high bulk density. The polymer powder is distinguished by very good flow properties.

The effect of the preactivation according to the invention of the metallocene by the aluminoxane, which is a strong Lewis acid, is not to reduce the metallocene and thereby to deactivate it irreversibly, but, on the contrary, to stabilize it. The known sensitivity to light of the metallocenes is also eliminated. At the same time, the requirement for (non-polymerizing) solvent or suspending agent is reduced by the preferred dissolution of the metallocene in the aluminoxane solution and the preferred polymerization in the liquid monomer.

The following examples are intended to illustrate the invention. The abbreviations have the following meanings:

VN=Viscosity number in $cm^3/g$, $M_w$=Weight average molecular weight $M_w/M_n$=Molecular weight distribution, determined by gel permeation chromatography, BD=Bulk density in $g/dm^3$ and II=Isotactic index, determined by $^{13}$C-NMR spectroscopy and $M_{iso}$=Length of the isotactic sequences, determined by $^{13}$C-NMR spectroscopy

EXAMPLE 1

A dry 16 $dm^3$ kettle was flushed with nitrogen and charged with 10 $dm^3$ of liquid propylene. 50 $cm^3$ of methylaluminoxane solution in toluene (corresponding to 40 mmol of aluminum, average degree of oligomerization of the methylaluminoxane, n=20) were then added, and the mixture was stirred for 15 minutes at 30° C. In parallel with this, 9 mg (0.02 mmol) of bisindenyldimethylsilylzirconium dichloride were dissolved in 25 $cm^3$ of methylaluminoxane solution in toluene (20 mmol of aluminum) and were preactivated by being allowed to stand for 15 minutes. The orange-red solution was then poured into the kettle. The polymerization system was brought to a temperature of 70° C. and was then kept at this temperature for 1 hour by suitable cooling. 2.0 kg of polypropylene were obtained. The activity of the metallocene was thus 100 kg of PP/mmol of Zr.hour.

VN=45 $cm^3/g$, $M_w$=35,000, $m_w/M_n$=2.1, BD=520 $g/dm^3$ and II=96.5%.

The Cl content and the Zr content in the polymer were below 1 ppm.

| Particle size distribution in the polymer | | |
|---|---|---|
| Sieve tray [μm] | Proportion in % | Total in % |
| <100 | 1.9 | 1.9 |
| 100–200 | 11.8 | 13.7 |
| 200–300 | 29.7 | 43.4 |
| 300–400 | 17.0 | 60.4 |
| 400–500 | 17.2 | 77.6 |
| 500–630 | 18.3 | 95.9 |
| 630–800 | 3.3 | 99.2 |
| >800 | 0.8 | 100.0 |

$d_{50} = 340$ μm, $s = \ln\frac{d_{50}}{d_{16}} = 0.48$

EXAMPLE 2

The procedure followed was analogous to that of Example 1, but only 4.5 mg (0.01 mmol) of bisindenyldimethylsilylzirconium dichloride were employed instead of 9 mg, and the polymerization time was 2 hours.

1.95 kg of polypropylene were obtained. The activity of the metallocene was thus 97.5 kg of PP/mmol of Zr.hour.

VN=48 $cm^3/g$. $M_w$=39,000, $M_w/M_n$=2.2, BD=500 $g/dm^3$ and II=97%. The Cl content and the Zr content in the polymer were below 0.5 ppm. Consequently, no decrease in the polymerization activity had taken place in the second hour of the polymerization.

| Particle size distribution in the polymer | | |
|---|---|---|
| Sieve tray [μm] | Proportion in % | Total in % |
| <100 | 2.0 | 2.0 |
| 100–200 | 3.1 | 5.1 |
| 200–300 | 5.4 | 10.5 |

-continued

| Particle size distribution in the polymer | | |
|---|---|---|
| Sieve tray [μm] | Proportion in % | Total in % |
| 300–400 | 6.1 | 16.6 |
| 400–500 | 7.9 | 24.5 |
| 500–630 | 14.0 | 38.5 |
| 630–800 | 13.9 | 52.4 |
| 800–1,000 | 17.6 | 70.0 |
| 1,000–1,250 | 21.5 | 91.5 |
| 1,250–2,000 | 8.3 | 99.8 |
| >2,000 | 0.2 | 100.0 |

$d_{50} = 760 \ \mu m, \quad s = \ln\frac{d_{50}}{d_{16}} = 0.67$

EXAMPLE 3

The procedure followed was analogous to that of Example 1, but 20 mg (0.045 mmol) of bisindenyldimethylsilylzirconium dichloride were employed and the polymerization temperature was 50° C.

1.0 kg of polypropylene were obtained. The activity of the metallocene was thus 22.2 kg of PP/mmol of Zr.H.

VN=60 cm$^3$/g, M$_w$=55,000, M$_w$/M$_n$=2.0, BD=300 g/dm$^3$ and II=97.3%; the polymer contained 4.1 ppm of Cl and 4 ppm of Zr.

EXAMPLE 4

The procedure was analogous to that of Example 1, but 20 mg (0.045 mmol) of bisindenyldimethylsilylzirconium dichloride were employed, the polymerization temperature was 50° C. and the polymerization time was 2 hours.

1.91 kg of polypropylene were obtained. The activity of the metallocene was 21.2 kg of PP/mmol of Zr.hour.

VN=62 cm$^3$/g, M$_w$=57,000, M$_w$/M$_n$=2.2, BD=310 g/dm$^3$ and II=97.0%; the polymer contained 2.5 ppm of Cl and 2 ppm of Zr. Consequently, no decrease in the polymerization activity took place in the second hour of the polymerization.

EXAMPLE 5

A dry 16 dm$^3$ kettle was flushed with nitrogen and charged with 10 dm$^3$ of liquid propylene. 100 cm$^3$ of methyl aluminoxane solution in toluene (corresponding to 80 mmol of aluminum, average degree of oligomerization n=20) were then added, and the mixture was stirred for 15 minutes at 30° C. In parallel with this, 7.5 mg (0.017 mmol) of bisindenyldimethylsilylzirconium dichloride were dissolved in 50 cm$^3$ of methyl aluminoxane solution in toluene (40 mmol content of aluminum), and were preactivated by being left to stand for 15 minutes. The orange-red solution was then poured into the kettle. The polymerization system was brought to a temperature of 70° C. and was then kept at this temperature for 1 hour by appropriate cooling. 2.94 kg of polypropylene were obtained. The activity of the metallocene was thus 172.9 kg of PP/mmol of Zr.hour.

VN=47 cm$^3$/g, M$_w$=40,000, M$_w$/M$_n$=1.9, BD=530 g/dm$^3$ and II=97.1% and the Cl content and Zr content of the polymer were less than 0.5 ppm.

| Particle size distribution in the polymer | | |
|---|---|---|
| Sieve tray [μm] | Proportion in % | Total in % |
| <100 | 2.5 | 2.5 |
| 100–200 | 4.6 | 7.1 |
| 200–300 | 7.4 | 14.5 |
| 300–400 | 35.9 | 50.4 |
| 400–500 | 40.0 | 90.4 |
| 500–630 | 7.8 | 98.2 |
| 630–800 | 1.1 | 99.3 |
| 800–1,000 | 0.6 | 99.9 |
| >1,000 | 0.1 | 100.0 |

$d_{50} = 390 \ \mu m, \quad s = \ln\frac{d_{50}}{d_{16}} = 0.23.$

Comparison Example A

A dry 16 dm$^3$ kettle was flushed with nitrogen and charged with 10 dm$^3$ of liquid propylene. 150 cm$^3$ of methylaliminoxane solution in toluene (corresponding to 120 mmol of aluminum, average degree of oligomerization n=20) were then added and the mixture was stirred for 15 minutes. 7.5 mg (0.017 mmol) of bisindenyldimethylsilylzirconium dichloride, dissolved in 50 cm$^3$ of toluene which had been dried over an Na/K alloy, distilled and saturated with argon were added to the mixture. The polymerization system was brought to a temperature of 70° C. and was kept at this temperature for 10 hours by supplying further heat. 0.21 kg of polypropylene was obtained. The activity of the metallocene was thus 1.24 kg of PP/mmol of Zr.hour.

VN=40 cm$^3$/g, M$_w$=26,400, M$_w$/M$_n$=1.9, BD=80 g/dm$^3$ and II=90.1%. 100% of the polymer had a particle size of <50 μm.

Comparison Example B

A dry 16 dm$^3$ kettle was flushed with nitrogen and charged with 10 dm$^3$ of liquid propylene. 7.5 mg (0.017 mmol of bisindenyldimethylsilylzirconium dichloride which had been dissolved in 50 cm$^3$ of toluene dried over an Na/K alloy, distilled and saturated with argon, and which had been combined with 150 cm$^3$ of methylaluminoxane solution in toluene (corresponding to 120 mmol of aluminum, average degree of oligomerization n=20) were then added. The polymerization system was brought to a temperature of 70° C. and was kept at this temperature for 10 hours by supplying further heat. 1.06 kg of polypropylene were obtained. The activity of the metallocene was 6.2 kg of PP/mmol of Zr.hour.

VN=43 cm$^3$/g, M$_w$=32,700, M$_w$/M$_n$=2.2, BD=100 g/dm$^3$ and II=95.6%. 100% of the polymer had a particle size of <50 μm.

Comparison Example C

A dry 16 dm$^3$ kettle was flushed with nitrogen and charged with 10 dm$^3$ of liquid propylene. 100 cm$^3$ of methylaluminoxane solution in toluene (corresponding to 80 mmol of aluminum, average degree of oligomerization n=20) were then added and the mixture was stirred for 15 minutes at 30° C. In parallel with this, 7.5 mg (0.017 mmol) of bisindenyldimethylsilylzirconium dichloride were dissolved in 50 cm$^3$ of toluene (0.34 mmol/dm$^3$). The toluene had previously been dried over an Na/K alloy, distilled and saturated with argon. 50 cm$^3$ of methylaluminoxane solution in toluene (40 mmol of aluminum) were added to this solution and were preactivated by being allowed to stand for 15 minutes. The solution was then poured into the kettle. The polymerization system was brought to a temperature of 70° C. and then kept at this temperature for 1 hour. 0.61 kg of polypropylene was obtained. The activity of the metallocene was 35.9 kg of PP/mmol of Zr.hour.

VN=43 cm$^3$/g, $M_w$=32,800, $M_w/M_n$=2.0, BD=305 g/dm$^3$ and II=92.1%.

| Particle size distribution | | |
|---|---|---|
| Sive tray [μm] | Proportion in % | Total in % |
| < 100 | 33.6 | 33.6 |
| 100–200 | 65.4 | 99.0 |
| >200 | 1.0 | 100.0 |

$d_{50}$ = 115 μm.

EXAMPLE 6

The procedure was analogous to that of Example 5, but 20 mg (0.045 mmol) of bisindenyldimethylsilylzirconium dichloride were employed. The polymerization temperature was 50° C.

1.82 kg of polypropylene were obtained. The activity of the metallocene was 40.4 kg of PP/mmol of Zr.hour.

VN=58 cm$^3$/g, $M_w$=53,000, $M_wM_n$=2.0, BD=320 g/dm$^3$ and II=98%; the polymer contained 2.1 ppm of Cl and 3 ppm of Zr.

EXAMPLE 7

The procedure was analogous to that of Example 5, but 20 mg (0.045 mmol) of bisindenyldimethylsilylzirconium dichloride were employed and the polymerization temperature was 35° C.

0.95 kg of polypropylene was obtained. The activity of the metallocene was 21.1 kg of PP/mmol of Zr.hour.

VN=74 cm$^3$/g, $M_w$=72,000, $M_w/M_n$=2.2, BD=160 g/dm$^3$ and II=98.3%; the polymer contained 4.4 ppm of Cl and 5 ppm of Zr.

EXAMPLE 8

The procedure was analogous to that of Example 5, but 40 mg (0.09 mmol) of bisindenyldimethylsilylzirconium dichloride were employed and the polymerization temperature was 20° C.

1.05 kg of polypropylene were obtained. The activity of the metallocene was 11.7 kg of PP/mmol of Zr.hour.

VN=90 cm$^3$/g, $M_w$=92,000, $M_w/M_n$=2.0, BD=150 g/dm$^3$ and II=98.5%; the polymer contained 5.8 ppm of Cl and 7 ppm of Zr.

Comparison Example D

The procedure was analogous to that of Comparison Example C, but 40 mg (0.09 mmol) of bisindenyldimethylsilylzirconium dichloride were employed and the polymerization temperature was 20° C.

0.16 kg of polypropylene was obtained. The activity of the metallocene was 1.78 kg of PP/mmol of Zr.hour.

VN=91 cm$^3$/g, $M_w$=91,000, $M_w/M_n$=2.0, BD=85 g/dm$^3$ and II=98%. 100% of the polymer had a particle size of <50 μm.

EXAMPLE 9

The procedure was analogous to that of Example 5, but 100 mg (0.223 mmol) of bisindenyldimethylsilylzirconium dichloride were employed. The polymerization temperature was 0° C.

1.47 kg of polypropylene were obtained. The activity of the metallocene was 6.6 kg of PP/mmol of Zr.hour.

VN=114 cm$^3$/g, $M_w$=115,000, $M_w/M_n$=1.9, BD=140 g/dm$^3$ and II=99.3%; the polymer contained 12 ppm of Cl and 11 ppm of Zr.

EXAMPLE 10

The procedure was analogous to that of Example 5, but 25 mg (0.056 mmol) of bisindenyldimethylsilylzirconium dichloride were employed, the polymerization temperature was 0° C. and the polymerization time was 5 hours.

1.62 kg of polypropylene were obtained. The activity of the metallocene was 5.8 kg of PP/mmol of Zr.hour.

VN=110 cm$^3$/g, $M_w$=112,000, $M_w/M_n$=2.0, BD=145 g/dm$^3$ and II=99.5%; the polymer contained 2.6 ppm of Cl and 4 ppm of Zr.

EXAMPLE 11

7.5 mg (0.017 mmol) of bisindenyldimethylsilylzirconium dichloride were dissolved in 50 cm$^3$ of methylaluminoxane solution in toluene (40 mmol of aluminum, average degree of oligomerization n=20), and the solution was allowed to stand for 100 hours with the exclusion of light (catalyst component (a)). A dry 16 dm$^3$ kettle was flushed with nitrogen and charged with 10 dm$^3$ of liquid propylene. 100 ml of methylaluminoxane solution in toluene (corresponding to 80 mmol of aluminum) were then added and the mixture was stirred for 15 minutes at 30° C. The orange-red solution of the catalyst component (a) was then poured into the kettle. The polymerization system was brought to a temperature of 70° C. and was then kept at this temperature for 1 hour by appropriate cooling. 2.79 kg of polypropylene were obtained. The activity of the metallocene was 164.1 kg of PP/mmol of Zr.hour.

VN=50 cm$^3$/g, $M_w$=42,000, $M_w/M_n$=2.0, BD=520 g/dm$^3$ and II=97.5%; the content of Cl and the content of Zr in the polymer were below 0.5 ppm.

Comparison Example E 7.5 mg (0.017 mmol) of bisindenyldimethylsilylzirconium dichloride were dissolved in 50 cm$^3$ of toluene which had been dried over an Na/K alloy, distilled and saturated with argon, and the solution was allowed to stand for 100 hours in daylight. 50 cm$^3$ of methylaluminoxane solution in toluene (corresponding to 80 mmol of aluminum, average degree of oligomerization n=20) were then added. The mixture was preactivated by being allowed to stand for 15 minutes (catalyst component (a)). In parallel with this, a dry 16 dm$^3$ kettle was flushed with nitrogen and charged with 10 dm$^3$ of liquid propylene. 100 cm$^3$ of methylaluminoxane solution in toluene (corresponding to 80 mmol of aluminum, average degree of oligomerization n=20) were then added and the mixture was stirred for 15 minutes at 30° C. The solution of the catalyst component (a) was then poured into the kettle. The contents of the kettle were brought to 70° C.

and kept at this temperature for 1 hour. 0.13 kg of polypropylene was obtained. The activity of the metallocene was 7.6 kg of PP/mmol of Zr.hour.

VN=45 cm$^3$/g, M$_w$=34,600, M$_w$/M$_n$=2.0, BD=120 g/dm$^3$ and II=95.1%. 100% of the polymer had a particle size of <50 μm.

EXAMPLE 12

The procedure was analogous to that of Example 11, but the methylaluminoxane/metallocene solution in toluene was exposed to daylight for 100 hours.

2.85 kg of polypropylene were obtained. The activity of the metallocene was 167.6 kg of PP/mmol of Zr.hour.

VN=48 cm$^3$/g, M$_w$=39,000, M$_w$/M$_n$=2.1, BD=52 g/dm$^3$ and II=97.4%.

Comparison Example F 7.5 mg (0.017 mmol) of bisindenyldimethylsilylzirconium dichloride were dissolved in 50 cm$^3$ of toluene which had been dried over an Na/K alloy, distilled and saturated with argon, and the solution was allowed to stand for 1 hour in daylight. 50 cm$^3$ of methylaluminoxane solution in toluene (corresponding to 80 mmol of aluminum, average degree of oligomerization n=20) were then added. The mixture was preactivated by allowing it to stand for 15 minutes. In parallel with this, a dry 16 dm$^3$ kettle was flushed with nitrogen and charged with 10 dm$^3$ of liquid propylene. 100 cm$^3$ of methylaluminoxane solution in toluene (corresponding to 80 mmol of aluminum, average degree of oligomerization n=20) were then added and the mixture was stirred for 15 minutes at 30° C. The solution of the catalyst component (a) was then poured into the kettle. The polymerization system was brought to a temperature of 70° C. and was then kept at this temperature for 1 hour. 0.41 kg of polypropylene was obtained. The activity of the metallocene was 24.1 kg of PP/mmol of Zr.hour.

VN=41 cm$^3$/g, M$_w$=31,000, M$_w$/M$_n$=2.0, BD=210 g/dm$^3$ and II=94.5%. 100% of the polymer had a particle size of 21 100 μm.

Comparison Example G

The procedure was as in Comparison Example F, but the toluene solution of the metallocene was allowed to stand for 100 hours in daylight before the methylaluminoxane was added.

No polypropylene was obtained from the polymerization; the catalyst system was thus completely inactive.

EXAMPLE 13

A dry 16 dm$^3$ kettle was flushed with nitrogen and charged with 10 dm$^3$ of liquid propylene. 100 cm$^3$ of methylaluminoxane solution in toluene (corresponding to 80 mmol of aluminum, average degree of oligomerization n=20) were then added and the mixture was stirred for 15 minutes at 30° C. In parallel with this, 6 mg (0.014 mmol) of ethylenebisindenylzirconium dichloride were dissolved in 50 cm$^3$ of methylaluminoxane solution in toluene (40 mmol of aluminum) and was preactivated by being allowed to stand for 15 minutes. The yellow solution was then poured into the kettle. The polymerization system was brought to a temperature of 70° C. and was kept at this temperature for 1 hour by appropriate cooling. 3.05 kg of polypropylene were obtained. The activity of the metallocene was 217.9 kg of PP/mmol of Zr.hour.

VN=32 cm$^3$/g, M$_w$=20,500, M$_w$/M$_n$=2.0, BD=540 g/dm$^3$ and II=96.4%.

| Particle size distribution in the polymer | | |
|---|---|---|
| Sieve tray [μm] | Proportion in % | Total in % |
| <100 | 2.5 | 2.5 |
| 100–200 | 3.5 | 6.0 |
| 200–300 | 7.1 | 13.1 |
| 300–400 | 16.1 | 29.2 |
| 400–500 | 27.3 | 56.5 |
| 500–630 | 34.0 | 90.5 |
| 630–800 | 8.8 | 99.3 |
| >800 | 0.7 | 100.0 |

$$d_{50} = 475 \text{ μm}, \quad s = \ln\frac{d_{50}}{d_{16}} = 0.38$$

EXAMPLE 14

The procedure was analogous to that of Example 13, but 10 mg (0.024 mmol) of ethylenebisindenylzirconium dichloride were employed. The polymerization temperature was 50° C.

2.83 kg of polypropylene were obtained. The activity of the metallocene was 117.9 kg of PP/mmol of Zr.hour.

VN=45 cm$^3$/g, M$_w$=37,400, M$_w$/M$_n$=1.9, BD=410 g/dm$^3$ and II=97.0%; the Cl content and the Zr content in the polymer were below 1 ppm.

| Particle size distribution | | |
|---|---|---|
| Sieve tray [μm] | Proportion in % | Total in % |
| <100 | 3.7 | 3.7 |
| 100–200 | 21.4 | 25.1 |
| 200–300 | 54.3 | 79.4 |
| 300–400 | 18.4 | 97.8 |
| >400 | 2.2 | 100 |

$$d_{50} = 250 \text{ μm}, \quad s = \ln\frac{d_{50}}{d_{16}} = 0.45$$

EXAMPLE 15

The procedure was analogous to that of Example 13, but 15 mg (0.036 mmol) of ethylenebisindenylzirconium dichloride were employed and the polymerization temperature was 35° C.

1.81 kg of polypropylene were obtained. The activity of the metallocene was 50.3 kg of PP/mmol of Zr.hour.

VN=54 cm$^3$/g, M$_w$=46,500, M$_w$/M$_n$=2.2, BD=330 g/dm$^3$ and II=97.0%; the polymer contained 1.8 ppm of Cl and 2 ppm of Zr.

EXAMPLE 16

The procedure was analogous to that of Example 13, but 20 mg (0.045 mmol) of ethylenebisindenylzirconium dichloride were employed. The polymerization temperature was 20° C.

1.05 kg of polypropylene were obtained. The activity of the metallocene was 23.3 kg of PP/mmol of Zr.hour.

VN=66 cm$^3$/g, M$_w$=62,400, M$_w$/M$_n$=2.0, BD=260 g/dm$^3$ and II=97.0%; the polymer contained 3.6 ppm of Cl and 4 ppm of Zr.

EXAMPLE 17

The procedure was analogous to that of Example 13, but 40 mg (0.096 mmol) of ethylenebisindenylzirconium dichloride were employed. The polymerization temperature was 0° C.

1.14 kg of polypropylene were obtained. The activity of the metallocene was 11.9 kg of PP/mmol of Zr.hour.

VN=76 cm$^3$/g, $M_w$=74,000, $M_w/M_n$=2.1, BD=200 g/dm$^3$ and II=98.1%; the polymer contained 6.3 ppm of Cl and 7 ppm of Zr.

EXAMPLE 18

The procedure was analogous to that of Example 13, but 15 mg (0.036 mmol) of ethylenebisindenylzirconium dichloride were employed and the polymerization temperature was 0° C. and the polymerization lasted for 5 hours.

1.96 kg of polypropylene were obtained. The activity of the metallocene was 10.9 kg of PP/mmol of Zr.hour.

VN=81 cm$^3$/g, $M_w$=80,200, $M_w/M_n$=2.0, BD=210 g/dm$^3$ and II=97.6%; the polymer contained 1.5 ppm of Cl and 2 ppm of Zr.

EXAMPLE 19

A dry 16 dm$^3$ kettle was flushed with nitrogen and charged with 10 dm$^3$ of liquid propylene. 100 cm$^3$ of methylaluminoxane solution in toluene (corresponding to 80 mmol of aluminum, average degree of oligomerization n=20) were then added, and the mixture was stirred for 15 minutes at 30° C. In parallel with this, 331 mg (1.0 mmol) of tetramethylethylenebiscyclopentadienyltitanium dichloride were dissolved in 50 cm$^3$ of methylaluminoxane solution (40 mmol) in toluene and were preactivated by being left to stand for 15 minutes. The solution was then poured into the kettle. The polymerization system was kept at 4° C. for 10 hours by appropriate cooling. 0.17 kg of polypropylene were obtained. The activity of the metallocene was 17 kg of PP/mol of Ti.hour.

$M_w$=119,500, $M_w/M_n$=2.4 and II=71%; length of the isotactic sequences, $n_{iso}$=4.6.

EXAMPLE 20

The procedure was analogous to that of Example 19, but 160 mg (0.281 mmol) of bis-(-)-neomenthylcyclopentadienylzirconium dichloride were employed, the polymerization temperature was 6° C. and the polymerization time was 8 hours. 1.50 kg of polypropylene were obtained. The activity of the metallocene was 0.67 kg of PP/mmol of Zr.hour.

$M_w$=25,800, $M_w/M_n$=2.7 and II=71%; length of the isotactic sequences, $n_{iso}$=3.5.

EXAMPLE 21

The procedure was analogous to that of Example 19, but 215 mg (0.379 mmol) of bis-(+)-neomenthylcyclopentadienylzirconium dichloride were employed, the polymerization temperature was 4° C. and the polymerization time was 8 hours. 1.67 kg of polypropylene were obtained. The activity of the metallocene was 0.55 kg of PP/mol of Zr.hour.

$M_w$=47,800, $M_w/M_n$=2.3 and II=74%; length of the isotactic sequences, $n_{iso}$=4.2.

EXAMPLE 22

The procedure was analogous to that of Example 19, but 200 mg (0.352 mmol) of bisneoisomenthylcyclopentadienylzirconium dichloride were employed, the polymerization temperature was 4° C. and the polymerization time was 6 hours. 1.45 kg of polypropylene were obtained; the activity of the metallocene was 0.69 kg of PP/mmol of Zr.hour.

$M_w$=24,400, $M_w/M_n$=2.8 and II=70%; length of the isotactic sequences, $n_{iso}$=3.8.

Comparison Example H

A dry 16 dm$^3$ kettle was flushed with nitrogen and charged with 10 dm$^3$ of liquid propylene and with 150 ml of methylaluminoxane solution in toluene (corresponding to 120 mmol of aluminum, average degree of oligomerization n=20). 200 mg (0.352 mmol) of bisneoisomenthylcyclopentadienylzirconium dichloride, dissolved in 50 cm$^3$ of toluene, were added to the mixture. The polymerization system was kept at 4° C. for 6 hours. 0.12 kg of polypropylene were obtained. The activity of the metallocene was 0.06 kg of PP/mmol of Zr.hour.

$M_w$=14,400, $M_w/M_n$=2.7 and II=71%; length of the isotactic sequences, $n_{iso}$=3.5.

What is claimed is:

1. A process for the preparation of a 1-olefin polymer by polymerizing a 1-olefin of the formula R—CH=CH$_2$ in which R is an alkyl group having 1 to 28 carbon atoms or copolymerizing these olefins together with ethylene at a temperature from −60° to 200° C., under a pressure of 0.5 to 60 bar, in solution, in suspension or in the gas phase and in the presence of a catalyst system comprising the reaction product obtained by dissolving a metallocene in a solution of an aluminoxane in an inert hydrocarbon wherein the aluminoxane is present in a concentration from approximately 1% by weight to the saturation limit.

2. The process as claimed in claim 1, wherein said metallocene is of the formula I

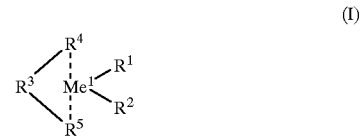

in which
Me$^1$ is a metal of the group IV b or Vb of the periodic system,
R$^1$ and R$^2$ are identical or different and are a C$_1$–C$_{10}$-alkyl group, a C$_6$–C$_{10}$-aryl group, a C$_2$–C$_{10}$-alkenyl group, a C$_7$–C$_{40}$-aralkyl group, a C$_8$–C$_{40}$-arylalkenyl group or a halogen atom,
R$^3$ is a linear C$_1$–C$_4$ hydrocarbon radical or a cyclic C$_4$–C$_6$ hydrocarbon radical wherein said hydrocarbon radicals optionally contain at least one heteroatom or R$^3$ is composed only of heteroatoms,
R$^4$ and R$^5$ are identical or different and are mononuclear or multinuclear hydrocarbon radicals together with the central atom can form a sandwich structure.

3. The process as claimed in claim 2, wherein Me$^1$ is titanium, zirconium, hafnium, vanadium, niobium or tantalum, R$^1$ and R$^2$ are identical or different and are a C$_1$–C$_3$-alkyl group, a C$_6$–C$_8$-aryl group, a C$_2$–C$_4$-alkenyl group, a C$_7$–C$_{10}$-arakyl group, a C$_8$–C$_{12}$-arylalkenyl group or a chlorine atom and R$^3$ is a linear C$_1$–C$_3$ hydrocarbon radical or a cyclic C$_4$–C$_6$ hydrocarbon radical which can optionally contain at least one heteroatom as a bridge unit in the chain.

4. The process as claimed in claim 2, wherein the $R^3$ is a —$CR^6_2$—, —O—, —S—, —SO—, —Se—, —SeO—, —$NR^6$—, —$PR^6$—, —$AsR^6$—, —$BR^6$—, —$AlR^6$, —$SiR^6_2$— and $GeR^6_2$, and $R^6$ is a hydrogen atom, a $C_6$–$C_{10}$-aryl group, a $C_1$–$C_{10}$-alkyl group, a $C_2$–$C_{10}$-alkenyl group, a $C_7$–$C_{40}$-arakyl group, a $C_8$–$C_{40}$-arylalkenyl group or a halogen atom.

5. The process as claimed in claim 4, wherein $R^6$ is a hydrogen atom, a $C_6$–$C_8$-aryl group, a $C_1$–$C_4$-alkyl group, a $C_2$–$C_4$-alkenyl group, a $C_7$–$C_{10}$-aralkyl group, a $C_8$–$C_{12}$-arylalkenyl group or a chlorine atom.

6. The process as claimed in claim 5, wherein $R^4$ and $R^5$ are identical and are indenyl, tetrahydroindenyl, cyclopentadienyl or heteroaromatic group ligands.

7. The process as claimed in claim 6, wherein $R^4$ and $R^5$ are identical and are indenyl and $Me^1$ is zirconium and $R^1$ and $R^2$ are identical and are a chlorine atom.

8. The process as claimed in claim 2, wherein the aluminoxane is a compound of the formula IV

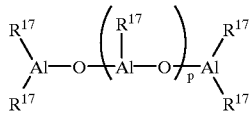
(IV)

for the linear type and/or the formula V

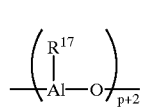
(V)

for the cyclic type, wherein $R^{17}$ denotes a $C_1$–$C_6$-alkyl group and p is an integer from 2 to 50.

9. The process as claimed in claim 8, wherein $R^{17}$ is methyl, ethyl or isobutyl and p is 15 to 30.

10. The process as claimed in claim 2, wherein $R^1$ and $R^2$ are identical
$R^3$ is —$(CR^6_2)_x$—, where x is 1 and where $R^6$ is a $C_6$–$C_{10}$-aryl group, a $C_1$–$C_{10}$-alkyl group, a $C_2$–$C_{10}$-alkenyl group, a $C_7$–$C_{40}$-aralkyl group, a $C_8$–$C_{40}$-arylalkenyl group or a halogen atom.

11. The process as claimed in claim 10, where $R^6$ is $C_1$–$C_4$-alkyl.

12. The process as claimed in claim 2, wherein $R^3$ is —$SiR^6_2$— wherein $R^6$ is a $C_6$–$C_{10}$-aryl group, a $C_1$–$C_{10}$-alkyl group, a $C_2$–$C_{10}$-alkenyl group, a $C_7$–$C_{40}$-aralkyl group, a $C_8$–$C_{40}$-arylalkenyl group or a halogen atom.

13. The process as claimed in claim 7, wherein $R^3$ is —$SiR^6_2$— wherein $R^6$ is a $C_6$–$C_{10}$-aryl group, a $C_1$–$C_{10}$-alkyl group, a $C_2$–$C_{10}$-alkenyl group, a $C_7$–$C_{40}$-aralkyl group, a $C_8$–$C_{40}$-arylalkenyl group or a halogen atom.

14. The process system as claimed in claim 2, wherein said metallocene is of the formula II

(II)

in which $Me^1$ is a metal of the group IV b or Vb of the periodic system, $R^7$ and $R^8$ are identical or different and are a halogen, $C_1$–$C_{10}$-alkyl group, a $C_6$–$C_{10}$-aryl group, a $C_2$–$C_{10}$-alkenyl group, a $C_7$–$C_{40}$-arylalkyl group, a $C_7$–$C_{40}$-arylalkyl group or a $C_8$–$C_{40}$-alkenylaryl group and $R^9$ and $R^{10}$ are identical or different and are substituted cyclopentadienyl radical.

15. The process as claimed in claim 2, wherein said metallocene is preactivated by the solution of the aluminoxane.

16. A process for preparing a 1-olefin polymer by polymerizing a 1-olefin of the formula R—CH=$CH_2$ in which R is an alkyl group having 1 to 28 carbon atoms or copolymerizing these olefins together with ethylene in the presence of a catalyst system comprising the reaction product obtained by dissolving a metallocene in a solution of an aluminoxane in an inert hydrocarbon wherein the aluminoxane is present in a concentration from approximately 1% by weight to the saturation limit.

* * * * *